United States Patent [19]
Lundell et al.

[11] Patent Number: 5,976,381
[45] Date of Patent: Nov. 2, 1999

[54] CHROMATOGRAPHIC PURIFICATION OF CYCLOSPORING USING A HIGH PRESSURE CARBON DIOXIDE ELUENT

[75] Inventors: Juhani Lundell, Ihala; Jarkko Ruohonen, Vanhalinna; Olli Aaltonen, Helsinki; Martti Alkio, Espoo; Anneli Hase, Espoo; Tapani Suortti, Espoo, all of Finland

[73] Assignee: Santen Oy, Tampere, Finland

[21] Appl. No.: 08/894,957

[22] PCT Filed: Mar. 1, 1996

[86] PCT No.: PCT/FI96/00120

§ 371 Date: Nov. 12, 1997

§ 102(e) Date: Nov. 12, 1997

[87] PCT Pub. No.: WO96/27607

PCT Pub. Date: Sep. 12, 1996

[30] Foreign Application Priority Data

Mar. 3, 1995 [FI] Finland ..................................... 950983

[51] Int. Cl.[6] ............................. B01D 15/08; A61K 38/12
[52] U.S. Cl. .......................... 210/656; 530/317; 435/71.1
[58] Field of Search .................................. 210/634, 656, 210/659; 530/317; 435/71.1

[56] References Cited

U.S. PATENT DOCUMENTS

| | | | |
|---|---|---|---|
| 4,478,720 | 10/1984 | Perrut | 210/659 |
| 4,581,166 | 4/1986 | Peter et al. | 530/144 |
| 5,256,547 | 10/1993 | Rudat et al. | 435/71.1 |

FOREIGN PATENT DOCUMENTS

| | | |
|---|---|---|
| 2108655 | 4/1996 | Canada . |
| 27 29 462 | 1/1979 | Germany . |
| 93/23394 | 11/1993 | WIPO . |

OTHER PUBLICATIONS

White, C.M., et al., Analysis of Pharmaceuticals and Other Solutes of Biochemical Importance . . . , Journal of High Resolution Chromatography & Chromatography Communications, vol. 11, Jan. 1988, pp. 94–98.

Wong et al. "Supercritical Fluid Chromatography for Therapeutic Drup Monitoring of Immunosuppressants: Selectivity for Cyclosporing A, FK 506 (Tacrolimus), and Rapamycin". Journal of Liquid Chromatography, 17(10), pp. 2093–2109, 1994.

*Primary Examiner*—W. L. Walker
*Assistant Examiner*—Richard W. Ward
*Attorney, Agent, or Firm*—Evenson, McKeown, Edwards & Lenahan, PLLC

[57] ABSTRACT

A process is provided for the preparation of pure cyclosporin which is purified chromatographically from a mixture of different cyclosporin forms and other substances prepared by fermentation. The process comprises feeding a mixture containing a desired form of cyclosporin with an eluent consisting of high pressure carbon dioxide and an adjuvant, into a chromatography column being packed with particles prepared of silica, and recovering from the eluent flow coming out of the chromatography column a fraction which contains the desired cyclosporin form in adequately pure form.

19 Claims, 6 Drawing Sheets

RUNNING TIME, min

CHROMATOGRAPHIC PURIFICATION OF CYCLOSPORING USING A HIGH PRESSURE CARBON DIOXIDE ELUENT

BACKGROUND AND SUMMARY OF THE INVENTION

The present invention relates to a process for the preparation of pure cyclosporin chromatographically from a mixture of different cyclosporins and other substances prepared by fermentation, using an eluent consisting essentially of high pressure carbon dioxide.

Cyclosporins are neutral, highly lipophilic, cyclic undekapeptides with a variable amino acid composition. At present, 25 different cyclosporin forms (A–Z) are known, from which the A-form has proved to be clinically the most valuable. Cyclosporins are produced by some fungi, e.g. *Cylindrocarpon lucidum, Trichoderma polysporum*, and various species of the genus Tolypocladium. Cyclosporins have been discovered to have not only of antibiotic activity, but also immunosuppressive properties, and they are currently used in the post-operative treatment of transplantation operations to prevent the rejection of the transplants. Cyclosporins are produced by fermenting fungal strains which produce great amounts of them. When mycclial extracts are obtained they usually contain different cyclosporin forms as a mixture. The desired form of cyclosporin has to be separated from the mixture obtained by fermentation by a purification process.

In the process currently in use, the separation of cyclosporin A is carried out by extracting the mycelial mass obtained by the fermentation first with methanol, whereafter the final separation is carried out in silica columns using different mixtures of organic solvents. The separation method is fairly slow and demands large chromatography columns with respect to the production volumes. Additionally, in a conventional process, great amounts of organic solvents must be handled, the purification and recycling of which is uneconomic and requires large equipment.

It is known that a substance which is in liquid form or in a supercritical state dissolves many compounds substantially better than the same substance in a gaseous state. Supercritical chromatography is indeed used to an ever-increasing amount to extract and separate various substances, especially in analytical applications (White et al., 1988, J. High Resolut. Chrom. & Chrom. Comm. 11:94–98).

In the U.S. Pat. No. 4,478,720, a process for fractionating of mixtures, and especially or purification of hydrocarbon mixtures by elution chromatography is disclosed. In the process, supercritical carbon dioxide without adjuvants is used as the eluent. In the international patent application WO 93/23394 optically pure S-timolol is produced from racemic R,S-timolol. Although the isomeric separation described in said application is in principle of the same kind as the separation disclosed in the present invention, the two processes differ from each other even for their grounds in that in the enantiomer separation of timolol is a question of chiral selectivity between the timolol enantiomers and the chiral column filling, whereas the present invention is based on the different polar interactions between the cyclosporins to be separated and the non-chiral column filling.

We have now found that the desired cyclosporin form can easily be obtained in pure form from a mixture of cyclosporin forms and other substances prepared by fermentation by feeding the mixture into a chromatography column with an eluent consisting of high pressure carbon dioxide and an adjuvant, and recovering from the eluent flow, the fraction which contains the desired form of cyclosporin in adequately pure form.

By the process of this invention any desired form of cyclosporin included in the starting mixture can be prepared in pure form. Preferably cyclosporin A or cyclosporin G is prepared.

The purity of cyclosporin meeting the drug requirements has to be at least 98.5 weight-%. By optimizing the process parameters cyclosporin meeting the drug requirements is directly obtained according to the process of the present invention from a certain part of the eluent flow.

An advantage of the process is in that the separation of the cyclosporin forms can be carried out continuously in phases so that the following batch of the mixture can be fed to the chromatography column soon after the previous batch, whereby the desired form of cyclosponrin meeting the drug requirements can continuously be recovered from the eluent flow coming out of the column. The purification process can thus be carried out rapidly and with small equipment with respect to the production rate.

In addition, the production process according to the invention is simple. It has only three main stages: feeding of the cyclosporin mixture to a chromatography column with an eluent consisting of carbon dioxide and an adjuvant, chromatographic separation of the desired cyclosporin form, and separation of the pure product from the eluent.

It is characteristic to the process of the invention that a mixture prepared by fermentation containing many forms of cyclosporin and other substances originating from the fermentation as extracted into a suitable solvent, e.g. toluene, is fed into the eluent flow consisting of high pressure carbon dioxide and an appropriate adjuvant. The eluent is fed into a chromatography column at a temperature of 20 to 100° C., preferably at the temperature of 20 to 60° C., and at an increased pressure, preferably at the pressure of 75 to 350 bar (7.5 to 35 MPa). A continuous eluent flow is running through the column. As an eluent carbon dioxide is used, to which an adjuvant or a modifying agent has been added, being e.g. a low molecular alcohol, preferably methanol or 2-propanol. A mixture of suitable low molecular alcohols can also be used. The amount of the adjuvant in the eluent is between 1 to 50, preferably 4 to 28 weight-%. The chromatography column has been packed with a solid filler, e.g. with silica particles or modified silica.

A further advantage of the process of the invention is also the fact that one can directly use as a starting material solutions which have been obtained by extracting the mycelial mass obtained by fermentation with suitable solvents, e.g. with methanol and toluene. These solutions may contain many kinds of components in addition to the cyclosporin forms to be separated. For instance pigments and other impurities originating from the cultivation are left over in the solution during the extraction. The cyclosporin mixture to be separated (mycelial extract) can further be dissolved in another solvent, e.g. toluene, dichloromethane or methanol, and this solution can be fed into the chromatography column.

An example of a solid filler which can be used is silica. The diameter of the silica particles can be from 5 to 200 $\mu$m, preferably from 5 to 45 $\mu$m, most preferably e.g. 10 $\mu$m, and the pore size from 60 to 120 Å. Examples of silica which can be used as the column filler are cyanopropyl silica and propylenediol silica. The column filler and the adjuvant of the eluent have to be selected so that the desired cyclosporin form is eluted sufficiently separated from the other forms of cyclosporin. When purifying cyclosporin A the preferable selection is silica filler together with a methanol or 2-propanol adjuvant.

In addition to the above mentioned parameters an economical realization requires the use of a correct loading ratio. The "loading ratio" of the column is the ratio (mg/g) of the total amount of cyclosporin forms fed into the column to the amount of the filling material of the column. A suitable loading ratio depends on the adjuvant on the eluent, and of the amount thereof. In a silica column, using 2-propanol adjuvant, the suitable loading ratio is e.g. from 1.5 to 4.4 mg/g. In a silica column using methanol adjuvant the suitable loading ratio is e.g. from 4.4 to 16.2 mg/g.

The eluent flow coming out from the chromatography column is monitored with a suitable detector, e.g. with an ultraviolet detector in the wave length region of 210 to 250 nm. The eluent flow coming out of the column is divided into temporally successive fractions so that the fraction containing the desired cyclosporin form is recovered. The pressure of the eluent flow fraction to be recovered is decreased, whereby the adjuvant and cyclosporin being dissolved therein are separated from the carbon dioxide, which is evaporated. The desired cyclosporin form is recovered from the adjuvant solution obtained by known processes of chemical technology.

One embodiment of the process of the invention is to perform the purification of the mixture containing the cyclosporin forms in several successive steps. In the first chromatographic purification step, a chromatography column can be packed with, for example, large silica particles. A suitable particle size may be e.g. 25 to 40 µm. In the first, coarse purification silica can be loaded with a fairly large amount of the mixture to be purified. A suitable loading ratio can be, e.g., 20 mg per g of silica. From the first chromatography step, a still impure fraction is recovered which, however, contains the main part of the desired cyclosporin form.

The coarsely purified product obtained from the first purification step is injected into a second chromatography column which has been packed with a high resolution silica. In the second chromatography step, a lower loading ratio is used, as well as a column which has been packed with silica having a fairly small particle size.

A chromatographical purification with two or more steps can be more advantageous with respect to the economy of the process than a one-step purification, e.g. in such a case in which the raw material mixture to be purified contains ingredients which stain the first chromatography column.

It is important that the process parameters are optimized so that the yield of the desired product meeting the drug requirements is as high as possible. In the following Examples those conditions are given in which cyclosporin meeting the drug requirements is advantageously obtained with high yield according to the present invention. In the experiments carried out, it is shown that the adjuvants (modifying agents) obvious to a person skilled in the art in the carbon dioxide eluent are not necessarily functional, but that only certain combinations of a column filling and an adjuvant cause such a separation that industrial production will be possible. In the Examples, it is also shown that by optimizing the process parameters the problematic impurities are made to elute ahead of the product which promotes the selectivity of the separation and makes the process technically and economically feasible.

DETAILED DESCRIPTION OF THE INVENTION

EXAMPLE 1

Figure 1:
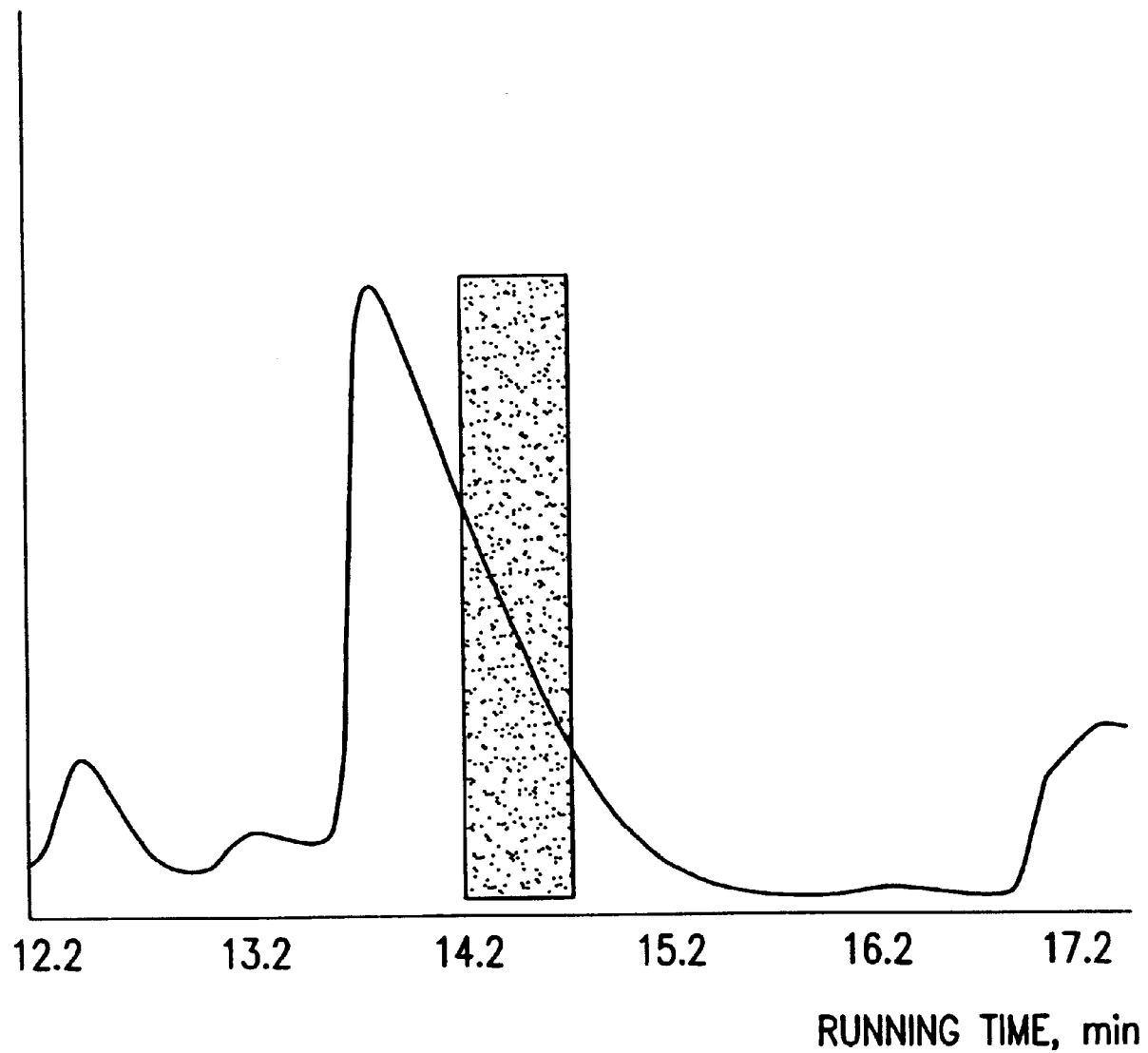
FIG. 1 Fractionating of toluene extract of cyclosporin. The shaded time region is the one where the purity of cyclosporin A recovered meets the drug requirements.

35 µl of mixture of cyclosporin forms containing several forms of cyclosporin as well as other substances dissolved in toluene, were fed, using an injection valve conventional in chromatographic methods, to a constant eluent flow. The composition of the eluent was: 81.1 weight-% of carbon dioxide and 18.9 weight-% of 2-propanol. In the toluene solution fed into the eluent the total concentration of cyclosporin forms was 426 mg/ml. The proportion of cyclosporin A in the cyclosporin forms present in the toluene solution was 22 weight-%. The pressure of the eluent flow was 200 bar and the temperature 50° C.. 4.1 g of the eluent was fed into the chromatography column per minute.

The eluent and the mixture of cyclosporin forms fed into it were fed into a chromatography column which had been packed with silica particles having a mean diameter of 10 µm, and the diameter of the pores of the particles was 60 Å. The diameter of the chromatography column was 10 mm, and the length of the silica filling of the column in the direction of the eluent flow was 250 mm. The amount of silica contained in the column was 7.9 g. The total amount of the cyclosporin forms fed into the column with the eluent calculated per the amount of silica was 1.9 mg/g silica.

The eluent flow coming out of the chromatography column was monitored with an ultraviolet detector, in a wave length region of 210 to 250 nanometers. The fraction of the eluent flow coming out of the column and containing the cyclosporin A form was divided into aliquots by feeding the eluent flow temporally successively into six receivers. The composition of each fraction was analyzed using the liquid chromatography method recommended by U.S. XXIII pharmacopoeia.

The analysis results showed that cyclosporin A can be separated as sufficiently pure only if a strictly limited fraction of the eluent flow containing it is recovered. In Table 1 the concentration of cyclosporin A in the fractions is given and in FIG. 1 the shaded region shows the section of the eluent flow which contains sufficiently pure cyclosporin A.

TABLE 1

Cyclosporin A concentrations in the fractions

| The mean collecting time of a fraction as counted from the feeding time to the column of the mixture to be separated, minutes | Concentration of cyclosporin A in the fraction weight-% |
|---|---|
| 13.80 | 33.00 |
| 14.13 | 96.95 |
| 14.40 | 99.06 |
| 14.66 | 99.03 |
| 14.94 | 97.98 |
| 15.22 | 96.00 |

Collecting of the eluent flow from the outlet part of the column was begun when 14.28 minutes had passed from the injection of the cyclosporin mixture, and stopped when 14.80 minutes had passed. 47.7 % of the amount of the cyclosporin A in the mixture to be separated was obtained as a product meeting the purity requirements.

Figure 2:
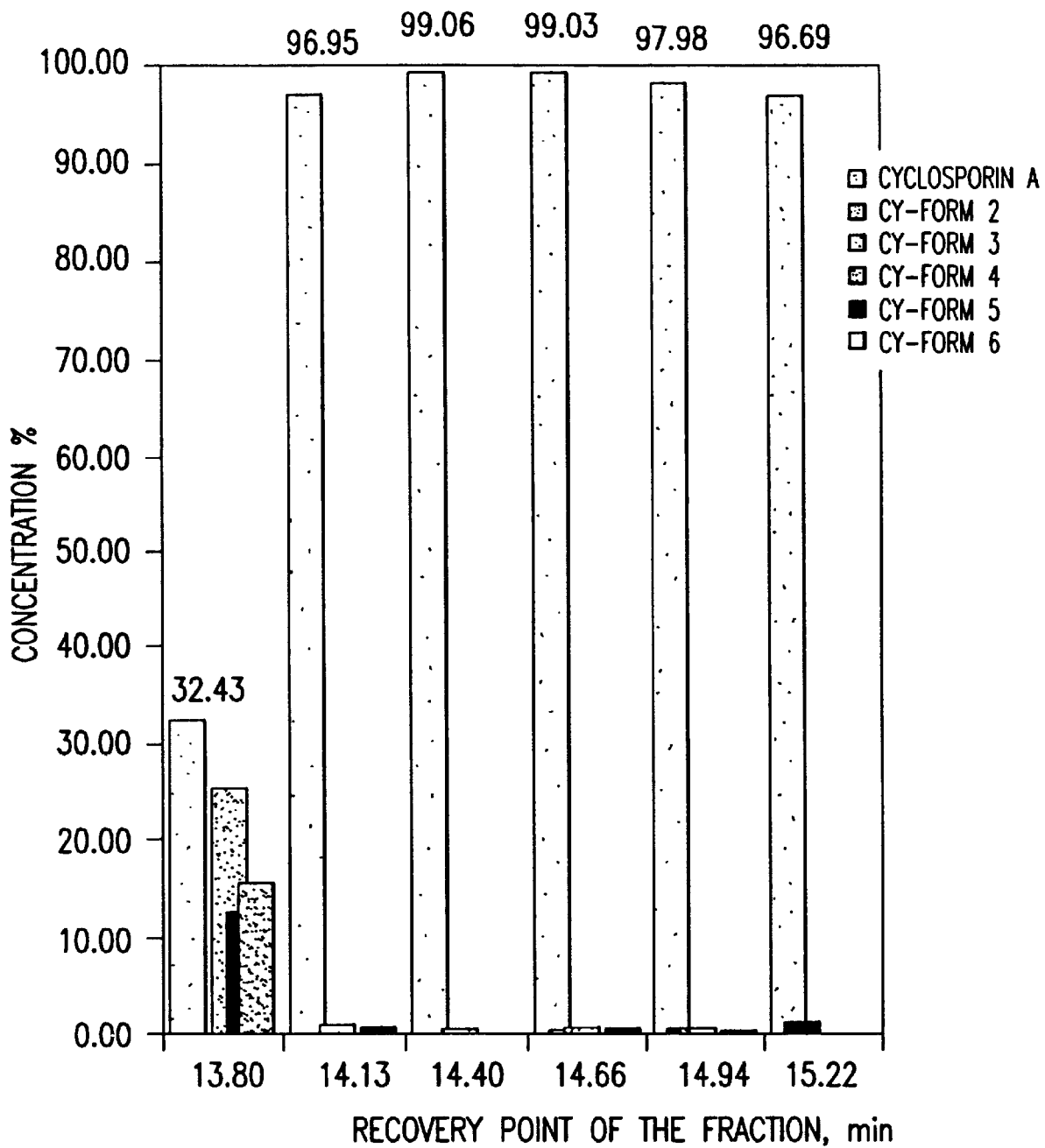
FIG. 2 Cyclosporin concentrations of the fractions recovered in the experiment according to Example 1.

The concentrations of cyclosporin forms contained in each fraction are given in FIG. 2. When collecting the eluent for the time of the whole chromatogram peak a product was obtained which had the cyclosporin A concentration of about 95%.

EXAMPLE 2
The Effect of the Adjuvant

Using the experimental procedure of Example 1, the mixture of cyclosporin forms dissolved in toluene described in Example 1 was injected into silica column with the dimensions of 4.0×150 mm. As eluent pure carbon dioxide was used, without additives. After two minutes toluene was perceived to elute, and thereafter no other substance was seen to elute out of the column. After about 60 minutes, the experiment was interrupted.

About 10% ethanol was added to carbon dioxide as an adjuvant. The cyclosporin forms were eluted then from the column after 5 to 15 minutes from the injection of the toluene solution of cyclosporins.

Using the experimental procedure of Example 1, the mixture of cyclosporin forms dissolved in toluene described in Example 1 was injected into silica column with the dimensions of 4.0×150 mm. About 5 weight-% of acetonitrile was added to the pure carbon dioxide eluent as an adjuvant. Within two hours from the injection of the toluene solution of cyclosporins nothing but toluene had been eluted from the column. The experiment was interrupted. 10% of ethanol was then added into the carbon dioxide eluent flow in place of acetonitrile. The elution of cyclosporin forms from the column began within about 10 minutes after beginning of the ethanolic eluent flow.

EXAMPLE 3

Using the experimental procedure described in Example 1, fractions containing cyclosporin A were prepared by varying the concentration of 2-propanol in the carbon dioxide eluent, and the amount of the cyclosporin to be fed into the column, i.e. the loading of the column. As a result, the yield of cyclosporin A meeting the drug requirements out of the amount of cyclosporin A fed into the column was monitored.

TABLE 2

Yield of pure cyclosporin A with different 2-propanol concentrations and column loading ratios.

| Test number | Concentration of 2-propanol in the carbon dioxide eluent weight-% | Loading ratio of the colunm = mg of cyclosporin mixture per g of silica mg/g | Yield of cyclosporin A meeting the drug requirements % |
|---|---|---|---|
| 3/1 | 18.9 | 8.7 | 0 |
| 3/2 | 24.6 | 8.7 | 0 |
| 3/3 | 18.9 | 4.4 | 43.7 |
| 3/4 | 21.8 | 4.3 | 43.6 |
| 3/5 | 24.6 | 4.3 | 64.5 |
| 3/6 | 27.3 | 4.3 | 59.4 |
| 3/7 | 21.5 | 1.5 | 92.5 |
| 3/8 | 21.5 | 8.7 | 0 |

EXAMPLE 4

In the experimental procedure described in Example 1, methanol was used as the adjuvant of the carbon dioxide eluent. The amount of methanol in the carbon dioxide as well as the amount of the cyclosporin mixture to be fed into the column were varied. As a result, the yield of cyclosporin A meeting the drug requirements calculated from the amount of cyclosporin A fed into the column in the mixture of cyclosporin forms was monitored.

TABLE 3

The yield of pure cyclosporin A by different methanol concentrations and column loading ratios.

| Test number | Concentration of methanol in the carbon dioxide eluent weight-% | Loading ratio of the colunm = mg of cyclosporin mixture per g of silica mg/g | Yield of cyclosporin A meeting the drug requirements weight-% |
|---|---|---|---|
| 4/1 | 12.2 | 13.1 | 0 |
| 4/2 | 10.6 | 16.2 | 36.3 |
| 4/3 | 12.2 | 8.7 | 43.6 |
| 4/4 | 14.5 | 8.7 | 0 |
| 4/5 | 12.2 | 4.4 | 67.0 |
| 4/6 | 17.5 | 4.4 | 38.8 |
| 4/7 | 23.2 | 4.4 | 0 |

EXAMPLE 5

In the experimental procedure described in Example 1, ethanol was used as the adjuvant of carbon dioxide. Ethanol was pumped into the carbon dioxide flow so that the concentration thereof was 17.5%. The yield of cyclosporin A meeting the drug requirements was 0% of the cyclosporin A included in the cyclosporin mixture.

EXAMPLE 6

In the experimental procedure described in Example 1, the amount of 2-propanol in the carbon dioxide was changed so that the concentration thereof was 13 weight percent. The period including cyclosporin G was selected as the cut-off point of the fraction. The recovery of the product began when 13.2 min from the injection moment had been passed, and stopped when 13.4 min from the injection moment had been passed. 18.5% of cyclosporin G meeting the drug requirements calculated from the amount of cyclosporin G fed into the column was obtained.

EXAMPLE 7

In the experimental procedure described in Example 1, the pressure, the temperature and the adjuvant concentration of the eluent flow fed into the column were varied. Methanol was used as adjuvant. The cyclosporin mixture to be fed into the column included 90 weight-% of cyclosporin A. The cyclosporin mixture was fed into the eluent flow going into the column as dissolved in dichloromethane.

TABLE 4

Yield of pure cyclosporin A at different pressures and temperatures and with different methanol concentrations.

| Test number | Pressure bar | Temperature °C. | Adjuvant concentration % | Yield of cyclosporin A meeting the drug requirements weight-% |
|---|---|---|---|---|
| 7/1 | 200 | 70 | 10 | 0 |
| 7/2 | 175 | 70 | 13 | 100 |
| 7/3 | 175 | 60 | 8 | 80 |
| 7/4 | 200 | 40 | 6 | 100 |
| 7/5 | 250 | 70 | 4 | 100 |
| 7/6 | 175 | 50 | 10 | 0 |

EXAMPLE 8

Other Solvent Alternatives of the Mixture to be Fed

By following the experimental procedure described in Example 1, methanol extract of the mycelia dissolved in methanol was injected into propylene diol column. To the carbon dioxide 5.1 weight-% of methanol was added as adjuvant. The most important forms of cyclosporin were eluted between 10 and 25 minutes.

According to the above described experimental procedure petroleum ether extract of mycelia diluted with toluene was injected into propylene diol column. The cyclosporin forms were separated between 15 and 25 minutes.

According to the experimental procedure described in Example 1, a mixture of four cyclosporin forms was injected into a silica column dissolved in dichloromethane (DKM) so that the total concentration thereof was 180 mg/ml. Each component was eluted separately, each by 100% yield.

The results obtained show that the cyclosporins to be fed can be dissolved in various solvents without decreasing the yields.

EXAMPLE 9

In the experimental procedure described in Example 1, the filling material of the chromatography column and the type of the adjuvant added into the carbon dioxide eluent were varied. As a result, the elution order of the cyclosporin forms was monitored.

TABLE 5

Elution order of cyclosporin forms when using different filling materials and adjuvants.

Figure 3:
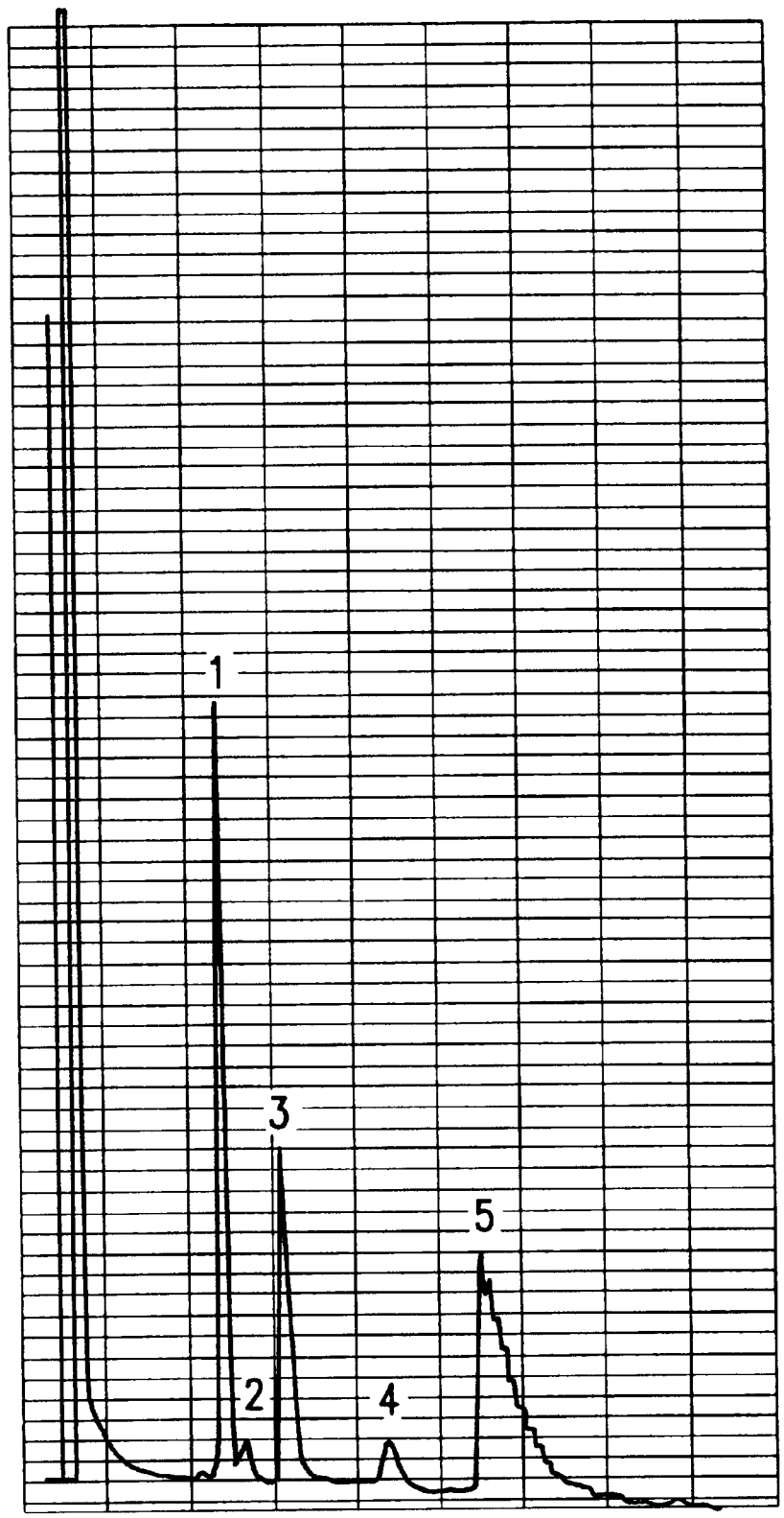
FIG. 3 The elution order of cyclosporin forms when the filling material of the column is cyanopropyl silica and the adjuvant of carbon dioxide is ethanol.
Figure 4:
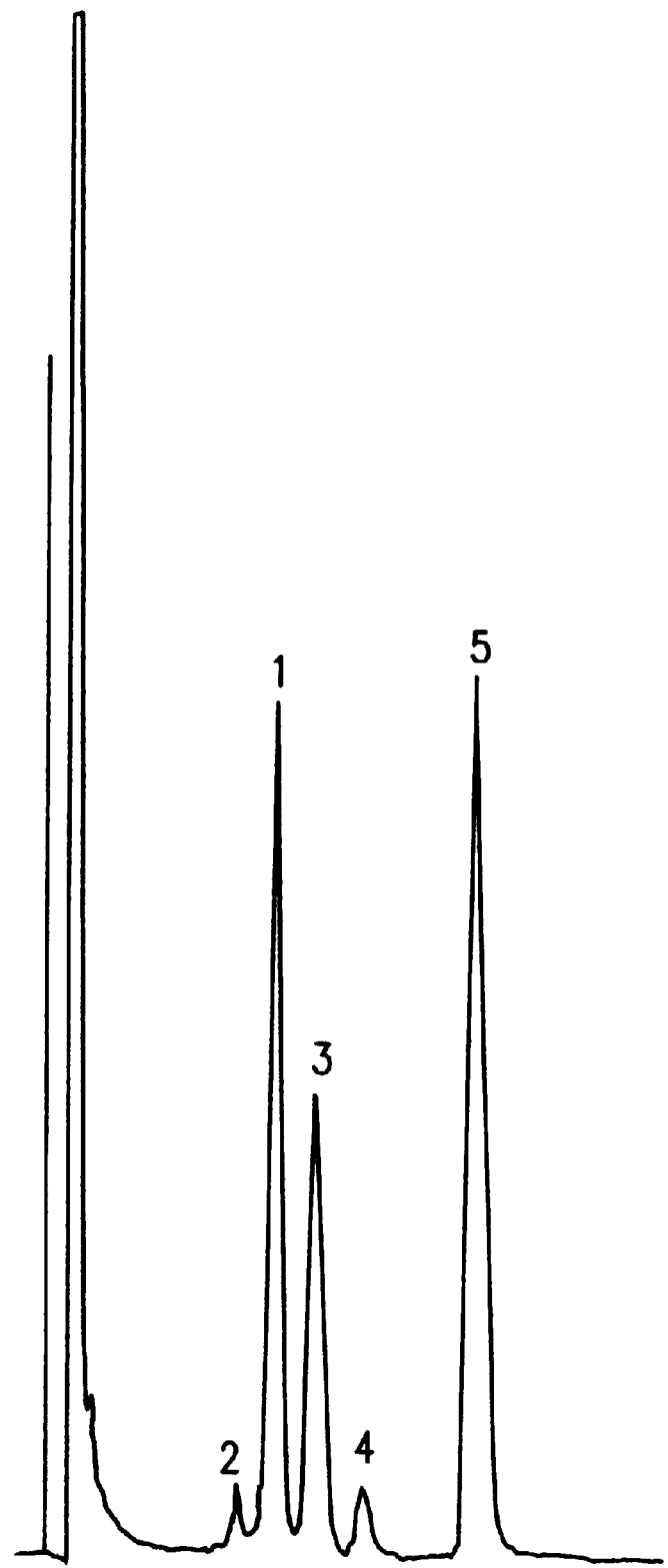
FIG. 4 The elution order of cyclosporin forms when the filling material of the column is propylenediol silica and the adjuvant of carbon dioxide is ethanol.

| Test number | Filling material of the column | Adjuvant of the carbon dioxide eluent | Elution order of cyclosporin forms | |
|---|---|---|---|---|
| 9/1 | Cyanopropyl silica | Ethanol | 1,2,3,4,5 | FIG. 3 |
| 9/2 | Propylenediol silica | Ethanol | 2,1,3,4,5 | FIG. 4 |

TABLE 5-continued

Elution order of cyclosporin forms when using different filling materials and adjuvants.

Figure 5:
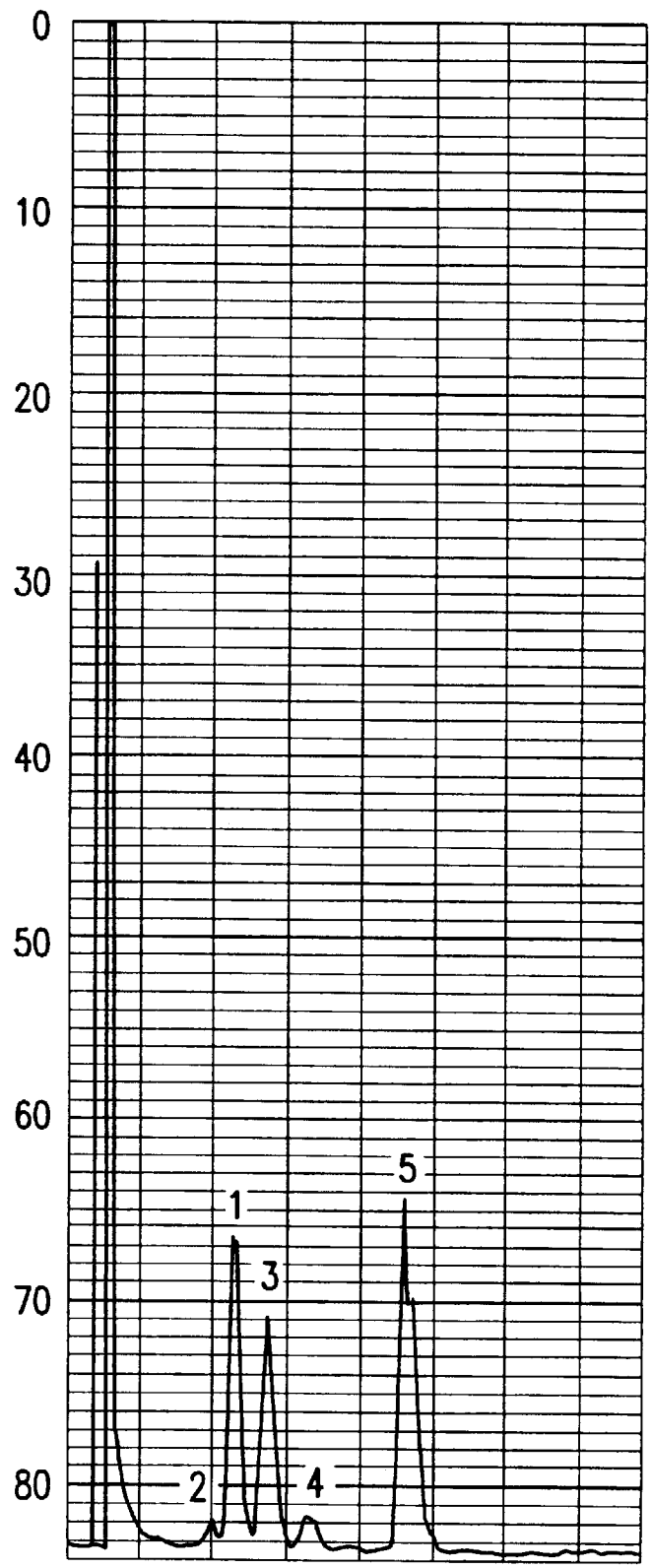
FIG. 5 The elution order of cyclosporin forms when the filling material of the column is propylenediol silica and the adjuvant of carbon dioxide is methanol.
Figure 6:
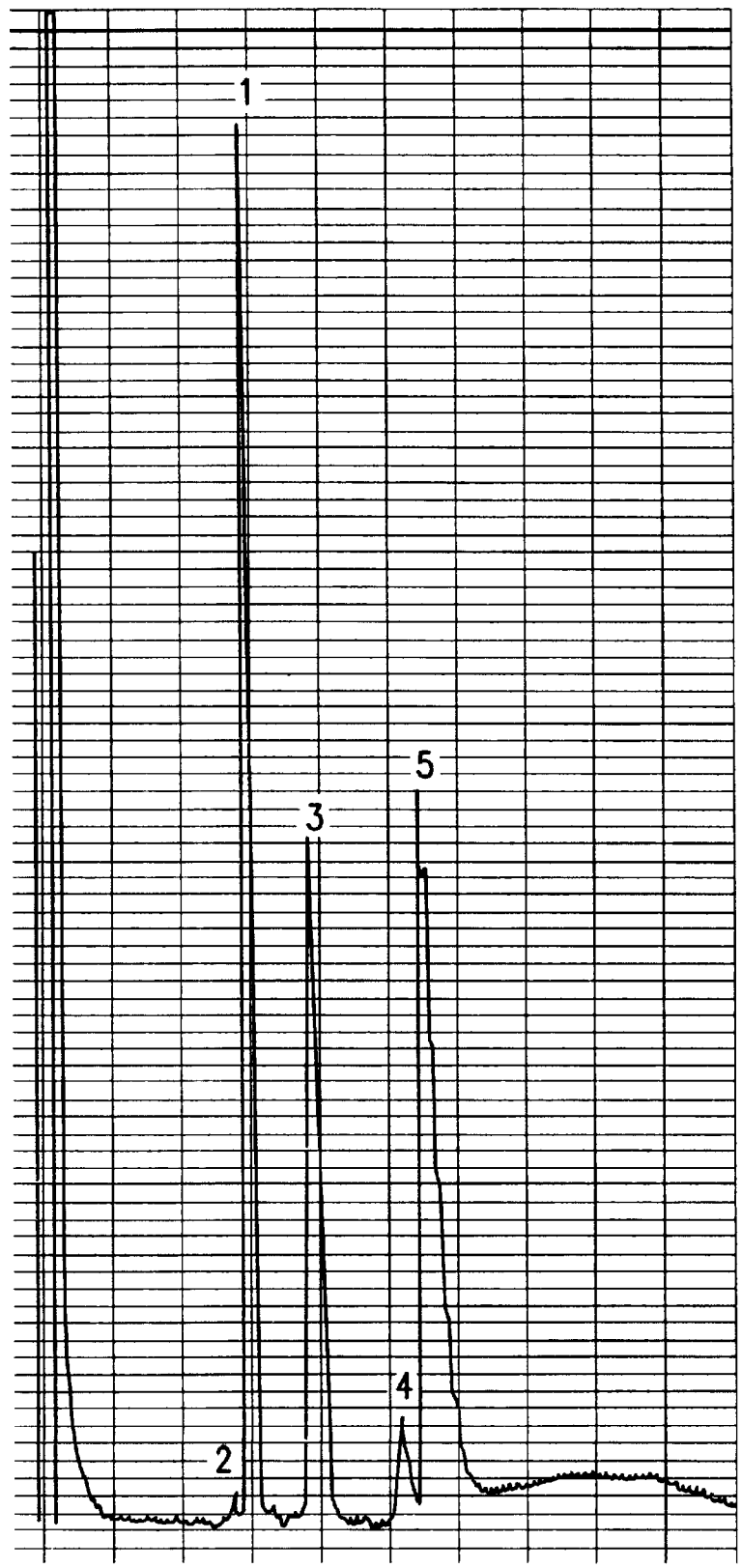
FIG. 6 The elution order of cyclosporin forms when the filling material of the column is silica and the adjuvant of carbon dioxide is methanol.

| Test number | Filling material of the column | Adjuvant of the carbon dioxide eluent | Elution order of cyclosporin forms | |
|---|---|---|---|---|
| 9/3 | Propylenediol silica | Methanol | 2,1,3,4,5 | FIG. 5 |
| 9/4 | Silica | Methanol | 2,1,3,4,5 | FIG. 6 |

It is seen from the analysis results that with a suitable combination of column filling and adjuvant the problematic impurities can be made to elute ahead of the desired form of cyclosporin.

EXAMPLE 10

In the experimental procedure described in Example 1, a mixture of cyclosporin forms was injected into a chromatography column which had been packed with silica particles having a particle size of 16 μm. The concentrations of cyclosporin A in the fractions recovered from the eluent flow coming out of the column were approximately the same as in Example 1.

EXAMPLE 11

Two-phase Purification

Toluene extract obtained from cyclosporin mycelial mass was injected into a chromatography column packed with silica particles having a diameter of 25 to 40 μm. The loading ratio was 20 mg per g of silica. All cyclosporin forms were eluted in the time range of 10 to 18 minutes, as one broad band. The eluent flow coming out of the column was divided into six temporally successive fractions. The cyclosporin A concentration of the material obtained in each fraction varied from 1 to 15%.

Four product fractions from the first chromatography purification containing the greatest amounts of cyclosporin A were pooled. They contained altogether 85% of the amount of cyclosporin A fed into the chromatography column.

The mixture obtained containing the cyclosporin forms was injected, using the experimental procedure, column and conditions described in Example 1, anew into a chromatography column within an eluent containing carbon dioxide. 75% of the product containing cyclosporin A which meets the drug requirements calculated from the amount of the cyclosporin A fed into the latter chromatography column was recovered from the latter chromatography purification.

We claim:

1. Process for the preparation of pure cyclosporin by chromatography from a mixture of different cyclosporin forms and other substances prepared by fermentation, comprising feeding a mixture containing a desired form of cyclosporin with an eluent consisting of high pressure carbon dioxide and an adjuvant, into a chromatography column being packed with particles prepared of silica, and recovering from the eluent flow coming out of the chromatography column a fraction which contains the desired cyclosporin form in adequately pure form.

2. Process according to claim 1, wherein the cyclosporin form is cyclosporin A or cyclosporin G.

3. Process according to claim 1 or 2, wherein the recovered cyclosporin form has a purity of over 98.5%.

4. Process according to claim 3, wherein a ratio of a total amount of cyclosporins fed into the column to an amount of filling of the column is from 1.5 to about 16.2 mg/g.

5. Process according to claim 3, wherein chromatography is carried out at a pressure of 200 bar and at a temperature of 50° C., and with an eluent containing about 78 weight-% of carbon dioxide and about 22 weight-% of 2-propanol as an adjuvant.

6. Process according to claim 3, wherein chromatography is carried out at a pressure of 200 bar and at a temperature of 40° C., and with an eluent containing about 94 weight-% of carbon dioxide and about 6 weight-% of methanol as an adjuvant.

7. Process according to claim 3, wherein the chromatography is carried out in two or more steps by injecting the mixture of cyclosporin forms into a first chromatography column, and injecting a prepurified product obtained therefrom into a second chromatography column, and recovering the desired cyclosporin form eluted therefrom.

8. Process according to any one of the claims 1, 2 and 4 to 7, wherein a ratio of a total amount of cyclosporins fed into the column to an amount of filling of the column is from about 1.5 to about 16.2 mg/g.

9. Process according to claim 8, wherein chromatography is carried out at a pressure of 200 bar and at a temperature of 50° C., and with an eluent containing about 78 weight-% of carbon dioxide and about 22 weight-% of 2-propanol as an adjuvant.

10. Process according to claim 8, wherein chromatography is carried out at a pressure of 200 bar and at a temperature of 40° C., and with an eluent containing about 94 weight-% of carbon dioxide and about 6 weight-% of methanol as an adjuvant.

11. Process according to any one of the claims 1, 2 and 4 to 9, wherein the chromatography is carried out at a pressure of 200 bar and at a temperature of 50° C., and with an eluent containing about 78 weight-% of carbon dioxide and about 22 weight-% of 2-propanol as an adjuvant.

12. Process according to any one of the claims 1, 2 and 4 to 9, wherein the chromatography is carried out at a pressure of 200 bar and at a temperature of 40° C., and with an eluent containing about 94 weight-% of carbon dioxide and about 6 weight-% of methanol as an adjuvant.

13. Process according to any one of the claims 1 or 2, wherein the chromatography is carried out in two or more steps by injecting the mixture of cyclosporin forms into a first chromatography column, and injecting a prepurified product obtained therefrom into a second chromatography column, and recovering the desired cyclosporin form eluted therefrom.

14. Process according to claim 1, wherein the column is packed with silica particles having a diameter of 5 to 45 $\mu$m and a pore size of 60 to 120 Å.

15. Process according to claim 1, wherein a chromatography separation is carried out at a pressure of 75 to 350 bar.

16. Process according to claim 1, wherein a chromatography separation is carried out in a temperature range of 20 to 100° C.

17. Process according to claim 1, wherein the eluent contains 99 to 50 weight-% of carbon dioxide and 1 to 50 weight-% of adjuvant.

18. Process according to claim 1, wherein the adjuvant used is a low molecular alcohol or a mixture of low molecular alcohols.

19. Process according to claim 18, wherein the adjuvant used is methanol or 2-propanol.

* * * * *